(12) United States Patent
Kawamura (10) Patent No.: US 9,192,725 B2
(45) Date of Patent: Nov. 24, 2015

(54) MEDICINE SYRINGE (71) Applicant: DAIKYO SEIKO, LTD., Tokyo (JP)

(72) Inventor: Hideaki Kawamura, Tokyo (JP)

(73) Assignee: DAIKYO SEIKO, LTD., Tokyo (JP)

( * ) Notice: Subject to any disclaimer, the term of this patent is extended or adjusted under 35 U.S.C. 154(b) by 386 days.

(21) Appl. No.: 13/672,388

(22) Filed: Nov. 8, 2012

(65) Prior Publication Data

US 2013/0144222 A1 Jun. 6, 2013

(30) Foreign Application Priority Data

Dec. 5, 2011 (JP) ................. 2011-266309

(51) Int. Cl.
*A61M 5/315* (2006.01)
*A61M 5/31* (2006.01)
*A61M 5/34* (2006.01)

(52) U.S. Cl.
CPC ....... *A61M 5/31515* (2013.01); *A61M 5/31531* (2013.01); *A61M 5/3137* (2013.01); *A61M 5/347* (2013.01)

(58) Field of Classification Search
CPC ............ A61M 5/3129; A61M 5/3134; A61M 5/31515; A61M 5/31531; A61M 5/347; A61M 5/3137
USPC .......... 604/68–72, 93.01, 181, 187, 192, 218, 604/263, 264, 272
See application file for complete search history.

(56) References Cited

U.S. PATENT DOCUMENTS

| 3,791,560 A | 2/1974 | Harris |
| 4,758,234 A | 7/1988 | Orentreich et al. |
| 5,795,337 A | 8/1998 | Grimard et al. |
| 6,149,629 A * | 11/2000 | Wilson et al. .................. 604/198 |
| 6,450,993 B1 * | 9/2002 | Lin ....................... A61M 5/282 604/199 |
| 7,713,244 B1 * | 5/2010 | Cherif Cheikh et al. ...... 604/218 |
| 2002/0161337 A1 | 10/2002 | Shaw et al. |
| 2003/0035744 A1 * | 2/2003 | Horita et al. ................... 417/460 |
| 2003/0163091 A1 * | 8/2003 | Bush, Jr. .............. A61M 5/3234 604/181 |
| 2004/0254540 A1 | 12/2004 | Shaw et al. |

(Continued)

FOREIGN PATENT DOCUMENTS

| EP | 1285675 | 2/2003 |
| GB | 2471726 A * | 1/2011 |

(Continued)

OTHER PUBLICATIONS

Japanese Office Action, Aug. 25, 2015; Japanese Patent Application No. 2011-266309 (3 pages).

*Primary Examiner* — Theodore Stigell
*Assistant Examiner* — Amber Stiles
(74) *Attorney, Agent, or Firm* — Hamre, Schumann, Mueller & Larson, P.C.

(57) ABSTRACT

A medicine syringe has a syringe barrel, piston and plunger rod. The syringe barrel is provided with a cylindrical main body defining therein a chamber to be filled with a medical solution, and an injection nozzle portion formed at an end portion of the main body and defining therein a hollow bore in communication with the chamber. The chamber and hollow bore have a total capacity of not greater than 0.5 mL. The chamber and hollow bore are formed such that the piston is slidable in a range of from 20 to 100 mm and is allowed to slide liquid-tight into the hollow bore beyond the chamber.

9 Claims, 3 Drawing Sheets (56) References Cited

U.S. PATENT DOCUMENTS

| | | |
|---|---|---|
| 2007/0060896 A1 | 3/2007 | Miller et al. |
| 2007/0088291 A1 | 4/2007 | Weilbacher |
| 2007/0191783 A1 | 8/2007 | Shaw et al. |
| 2007/0197977 A1* | 8/2007 | Shue et al. .................... 604/218 |
| 2008/0195059 A1* | 8/2008 | Sudo et al. .................... 604/239 |
| 2010/0130961 A1* | 5/2010 | Tucker .......................... 604/518 |

FOREIGN PATENT DOCUMENTS

| | | |
|---|---|---|
| JP | 08-010327 | 1/1996 |
| JP | 2003-509082 | 3/2003 |
| JP | 2006-272009 | 10/2006 |
| JP | 2009-506879 | 2/2009 |
| WO | WO 01/60435 | 8/2001 |
| WO | WO 2007/027585 | 3/2007 |

* cited by examiner

MEDICINE SYRINGE

CROSS-REFERENCE TO RELATED APPLICATION

This application claims the priority of Japanese Patent Application 2011-266309 filed Dec. 5, 2011, which is incorporated herein by reference.

BACKGROUND OF THE INVENTION

1. Field of the Invention

This invention relates to a syringe useful with a medicine, and specifically to a medicine syringe having a piston stroke long enough to facilitate its use even when the internal capacity of a syringe barrel is small and allowing only a small amount of a medical solution to remain in the syringe barrel upon completion of an injection of the medical solution by sliding a piston via a plunger rod.

2. Description of the Related Art

A syringe for use with a medicine varies in capacity and shape depending on its application. In particular, prefilled syringes which are finding increasing utility in recent years have been proposed in diverse designs and sizes, because they have been filled with medical solutions upon distribution from pharmaceutical makers and can hence be designed in shapes and capacities suited for the administration of the medical solutions. On the other hand, there has been a move in recent years toward smaller dose sizes. Keeping in step with this move, syringes to be used are also desired to meet this move toward smaller dose sizes. From the production technology, however, there is generally a restriction to a move toward smaller syringes, because the production of such smaller syringes is difficult. It is, therefore, a current practice to meet the move toward smaller dose sizes, for example, by filling a syringe of 3 mL capacity with a medical solution as little as only one third of its full capacity when desired to store 1 mL of the medical solution.

For the purpose of making more accurate a dose to be administered in addition to the economical viewpoint, there is also a long-standing desire to decrease a medical solution that remains in a syringe after the use of the medical solution, and numerous proposals have been made in this respect. For example, U.S. Pat. No. 5,795,337 to Jean Pierre Grimard discloses a piston-like stopper for use in a syringe barrel. In order to minimize a dead space in which a medical solution enters and is held unusable, the piston-like stopper is provided on a distal end of a stopper main body with a distally-directed, conically-shaped projection and is also provided with at least one elongate discontinuity (e.g., a raised rib, recessed grove, or the like) running along the conically-shaped projection. When a piston-like stopper is formed in such an intricate shape, however, the projection may not always be surely inserted at a distal end thereof into a passageway arranged at a distal end of the syringe barrel, and therefore, the occurrence of malfunction is concerned. For use in a syringe of such an extremely small capacity as a total capacity of not greater than 0.5 mL to which the present invention is directed as will be described subsequently herein, a piston itself is of an extremely small size. Such an extremely small piston is accompanied by a problem in that it can be hardly molded or otherwise formed or worked into such an intricate shape as proposed above and, even if good results are obtained with a usual size, the piston of the usual size cannot be applied as it is.

SUMMARY OF THE INVENTION

Under the above-described circumstances, syringes for use in today's plastic surgeries and ophthalmological treatments are used in such a way that an extremely small volume of a medical solution is injected in a plurality of portions at different locations. Especially in such a case, there is a desire for an easy-to-use syringe that makes it possible to appropriately administer a medical solution in extremely small volumes. In the course of a detailed study conducted in an attempt to meet such a desire, the present inventor came to recognize the existence of a problem as will be described hereinafter. Under the current situation, the administration in the above-described case is often performed in such a manner that a medical solution is filled, for example, in a syringe of 3 mL capacity to only one third of its full capacity as mentioned above. When the medical solution is administered in such a manner, however, the piston stroke with which the syringe is inherently provided becomes naturally shorter. As a consequence, the sensation to push in a plunger rod becomes weaker and, when desired to visually confirm a positional change of the piston, the piston stoke is too short to confirm even the positional change of the piston. The present inventor found that the above-mentioned shortcoming becomes a cause of giving significant uncertainty to the user as to whether or not the administration of the medical solution has been surely performed, and then became aware that it is important to solve the shortcoming. As another problem, the medicinal efficiency per unit volume of a medical solution has increased with the move toward smaller dose sizes. To make a dose more accurate, the matter of the amount of a medical solution remaining in a syringe after administration has become important than ever before. Moreover, the price of a medical solution per unit volume has risen with the move toward smaller dose sizes. From the economic significance, there is also an ever increasing desire to decrease the amount of a medical solution that remains in a syringe after use.

The present invention has, therefore, been made to meet the move toward extremely small internal capacities and to solve the problems which cannot be overcome by the conventional syringes. More specifically, an object of the present invention is to provide a syringe, which has a piston stroke long enough to facilitate its use, and moreover, allows a medical solution to remain only in an extremely small amount after administration.

The above-described object can be achieved by the present invention to be described hereinafter. Described specifically, to solve the above-described problems, the present invention provides, in one aspect thereof, a medicine syringe having a syringe barrel, piston and plunger rod, said syringe barrel being provided with a cylindrical main body defining therein a chamber to be filled with a medical solution, an injection nozzle portion for injecting the medical solution, said injection nozzle portion being formed at an end portion of the main body and defining therein a hollow bore in communication with the chamber, an opening formed at an opposite end portion of the main body for receiving the piston and plunger, and a flange portion, and said plunger rod being in a form of a rod having the piston arranged at an end portion thereof and a plunger flange formed at an opposite end portion thereof, wherein the chamber in the main body and said hollow bore in the injection nozzle portion have a total capacity of not greater than 0.5 mL, and the chamber and hollow bore are formed such that the piston is slidable in a range of from 20 to 100 mm and is allowed to slide liquid-tight into the hollow bore of the injection nozzle portion beyond the chamber located in the main body.

Preferably, the chamber and hollow bore have a same diameter.

The injection nozzle portion may preferably be further provided with a structure that enables to fit a syringe needle to the injection nozzle portion. The structure that enables to fit the syringe needle may be, for example, a Luer lock fitting for fixedly securing the syringe needle, with a female Luer lock fitting being more preferred.

The medicine syringe may further comprise a syringe needle integrally fitted to the injection nozzle portion. The injection nozzle portion may preferably be further provided with a Luer lock fitting for fixedly securing a needle shield to protect the syringe needle, with a female Luer lock fitting being more preferred.

The medical solution may preferably remain in an amount of not greater than 10 µL, in the syringe barrel upon completion of an injection of the medical solution by sliding the piston via the plunger rod. The flange portion of the syringe barrel may preferably extend out over a length of from 15 to 50 mm from the opposite end portion.

Preferably, the plunger rod and piston may be integrally molded. The medicine syringe may preferably further comprise a main body reinforcement formed over a joint area between the main body and the flange portion.

The syringe barrel may be formed, for example, of a cyclic olefin resin.

According to the present invention, there is provided a syringe, which is useful with a medicine, has a piston stroke long enough to facilitate its use even when its internal capacity is small, and allows only a small amount of a medical solution to remain.

DETAILED DESCRIPTION OF PREFERRED EMBODIMENTS

With reference to the accompanying drawings showing preferred embodiments for practicing the present invention, the present invention will next be described in further detail.

Figure 1:
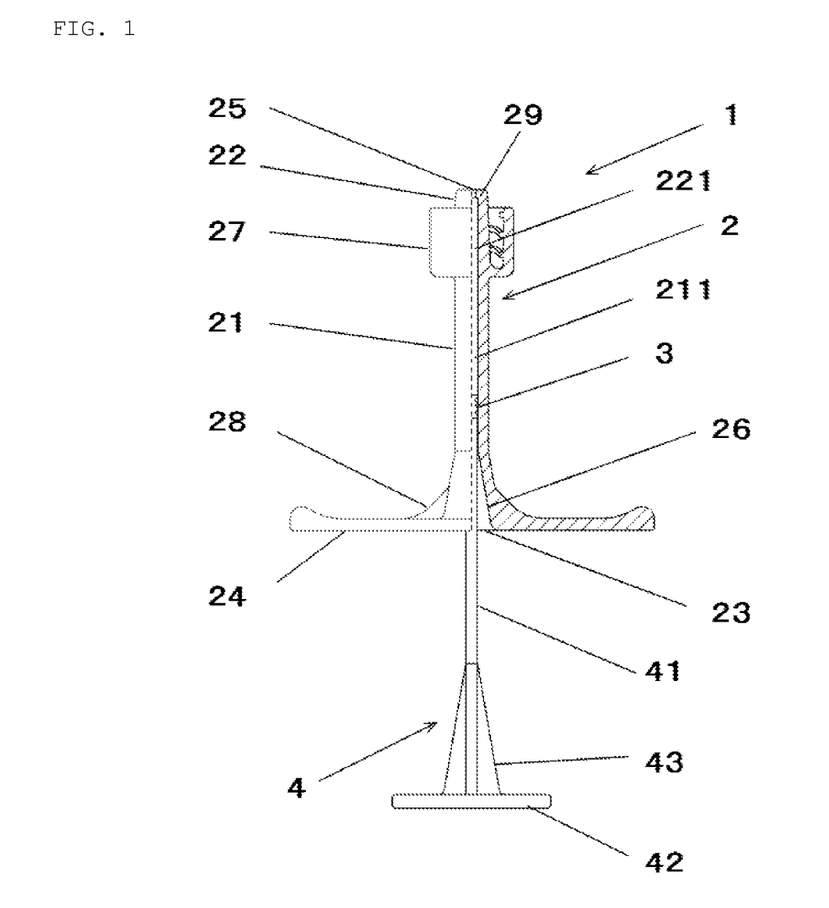
FIG. 1 is a schematic view for de scribing a medicine syringe according to a first embodiment of the present invention, in which some parts are shown in cross-section and a plunger rod has been inserted into a chamber of a syringe barrel through an opening of the syringe barrel.

As shown in FIG. 1, a medicine syringe 1 according to a first embodiment of the pre sent invention is constructed of a substantially cylindrical syringe barrel 2, a substantially cylindrical piston 3 configured to be slidable liquid-tight in a space formed in the syringe barrel 2 and to be filled with a medical solution, and a plunger rod 4 with the piston arranged at an end portion (distal end portion) thereof. These members will hereinafter be described in detail.

The syringe barrel 2 shown in FIG. 1 is constructed of a cylindrical main body 21, an injection nozzle portion 22 formed at an end portion (distal end portion) of the main body 21 and having a structure to enable the fitting of an unillustrated syringe needle, an opening 23 formed at an opposite end portion of the main body 21 to receive the piston and plunger rod, and a flange portion 24 formed in continuation with both side edges of the opening 23. The flange portion 24 of the syringe barrel may preferably have a length of from 15 to 50 mm from each of the side edges of the opening 23. To prevent the unillustrated syringe needle from accidentally separating from the injection nozzle portion 22, the present invention may preferably include, for example, a Luer lock fitting, specifically a female Luer lock fitting 27 formed surrounding an outer circumference of the injection nozzle portion 22 as shown in FIG. 1.

The syringe barrel 2 is provided with the space (hereinafter called a "chamber 211") formed in the main body 21 so that the medical solution can be filled in. By pushing the plunger rod 4 into the chamber 211 of the main body 21 of the syringe barrel, the piston 3 arranged at the distal end of the plunger rod 4 is operated. By this operation of the piston 3, the filled medical solution is injected from an injection port 25 arranged at the injection nozzle portion 22. In the medicine syringe according to the present invention, the total volume of a medicinal solution to be filled in its syringe barrel is required to be 0.5 mL or smaller. Therefore, the inner diameter of the chamber 211 of the main body 21 is far smaller than the corresponding dimensions in conventional syringes, and is designed smaller than approx. 3.925 mm which is the minimum outer diameter of an injection nozzle under ISO 594/1 specifications on injection nozzles adopted in general syringes. For example, the inner diameter may preferably be a little smaller than the outer diameter of the piston, for example, from 1.0 to 3.0 mm. The inner diameter may preferably be uniform along the length of the chamber 211, but for reasons such as molding convenience and the like, the chamber 211 may be in a flared form such that its inner diameter gradually increases toward the flange portion 24.

As shown in FIG. 1, the main body 21 of the syringe barrel 2, said main body 21 having the chamber 211 of such shape and dimensions as described above, continues to the injection nozzle portion 22, and the injection nozzle portion 22 is provided with the injection port 25 for injecting out the medical solution via the unillustrated syringe needle. In the first embodiment shown in FIG. 1, the injection port 25 is internally provided with a reduced diameter portion 29 into which the piston 3 cannot advance. This reduced diameter portion 29 is formed to prevent the piston 3 from falling off the injection port 25 when the piston 3 is slid in a direction to inject the medical solution.

In the first embodiment shown in FIG. 1, the diameter of the chamber 211 of the main body 21 and a hollow bore 221 formed in the injection nozzle portion 22 are, therefore, the same up to the reduced diameter portion 29 arranged inside the injection port 25, so that the piston 3 is allowed to slide liquid-tight into the injection nozzle portion 22 beyond the chamber 211 located in the main body 21 of the syringe barrel 2. As the total capacity, which may hereinafter be called simply "capacity" for the sake of brevity, of the chamber in the main body and the hollow bore in the injection nozzle portion of the medicine syringe according to the present invention is not greater than 0.5 mL, the syringe barrel is small in diameter and the flange portions are thin in thickness. As shown by way of example in FIG. 1, it is, therefore, preferred to form main body reinforcements 28 over joint areas between the main body 21 and the flange portion 24 at the opposite side edges of the opening 23, respectively.

Figure 3:
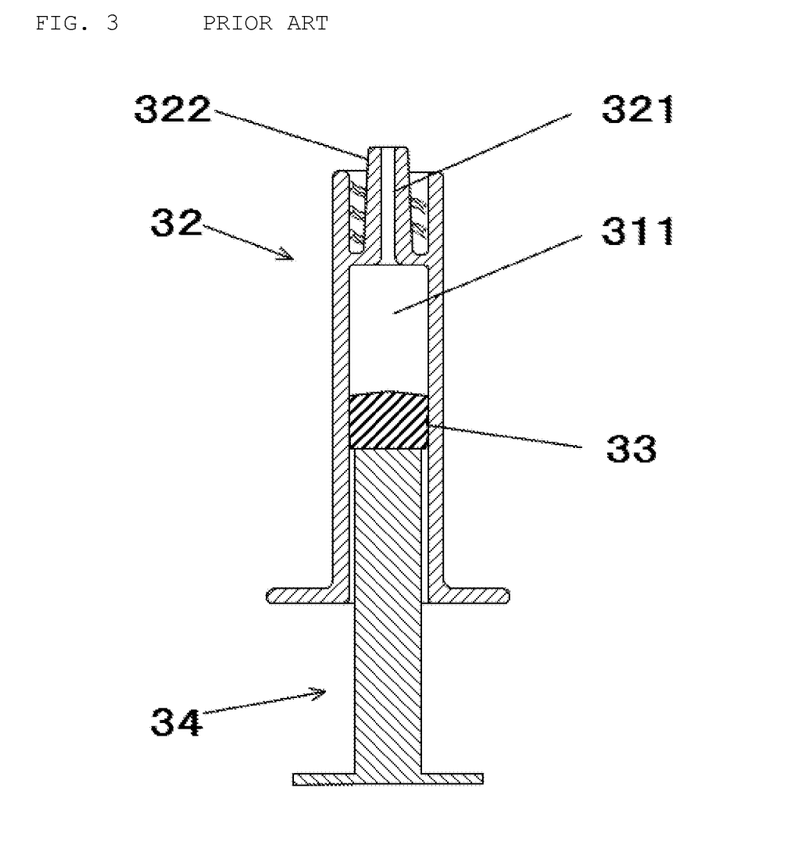
FIG. 3 is a schematic cross-sectional view of a conventional medicine syringe.

Referring next to FIG. 3, a conventional medicine syringe will be described. In the conventional medicine syringe, the diameter of a chamber 311 in a main body of a syringe barrel 32 is greater than the diameter of a hollow bore 321 at a proximal end portion of an injection nozzle portion 322. Through the chamber 311 in the main body of the syringe barrel 32, a piston 33 can slide to inject a medical solution filled in the chamber 311. However, the piston 33 cannot advance into the hollow bore 321 in the injection nozzle portion 322 so that the medical solution in the hollow bore 321 cannot be injected out. A step, therefore, exists as a boundary between the chamber 311 and the hollow bore 321. In the syringe barrel according to the present invention, on the other hand, a boundary such as a step as observed in the conventional medicine syringe does not exist between the chamber 211 in the main body 21 and the hollow bore 221 in the injection nozzle portion 22 of the syringe barrel 2 as shown in FIG. 1. The piston 3 can, therefore, slide up to the reduced diameter portion 29 in the hollow bore 221 of the injection nozzle portion 22. Owing to such a structure, the medicine syringe 1 according to the present invention has made it possible to extend a stroke (movable range) of the piston to the inside of the hollow bore 221 of the injection nozzle portion 22, and hence, to be provided with a long stroke. When an extremely small amount of a medical solution is administered with the conventional medicine syringe, it is difficult to confirm whether or not the administration has been completed. On the other hand, the user of the medicine syringe 1 according to the first embodiment of the present invention can clearly have an actual sensation of performing administration of the medical solution during the operation of the plunger rod 4. Described specifically, the progress of the administration of the medical solution can be precisely confirmed by the eyes depending on variations in the position of the plunger rod 4. In addition, the piston 3 is allowed to slide liquid-tight to the position of the reduced diameter portion 29 arranged inside the injection port 25 of the injection nozzle portion 22. When the extremely small amount of the medical solution is administered using the medicine syringe 1 according to the first embodiment of the present invention, the medical solution that remains in the syringe barrel 2 upon completion of the administration is practically found only in the hollow bore 221 at the position of the reduced diameter portion 29. The syringe barrel 2 can, therefore, make the amount of the medical solution, which remains therein upon completion of administration, significantly smaller than the syringe barrel 32 of the conventional medicine syringe.

The length of the reduced diameter portion 29 as measured in the axial direction of the syringe barrel 2 may be set at from 0.2 to 2.0 mm or so, preferably from 0.5 to 1.2 mm or so. On the other hand, the inner diameter of the reduced diameter portion 29 may be set at from 0.2 to 1.2 mm or so, preferably from 0.5 to 1.0 mm or so. Taking a 0.05-mL medicine syringe (axial length and inner diameter of the reduced diameter portion 29: 1.0 mm and 0.8 mm) as an example, the volume of the hollow bore 221 at the reduced diameter portion 29 can be calculated to be approx. 0.50 mm$^3$, which is about 1/26 of the corresponding volume of 13.3 mm in a conventional small-capacity medicine syringe (capacity: 3 mL, length of an injection nozzle portion: 10.0 mm, hollow bore in the injection nozzle portion: 1.3 mm). This means that according to the medicine syringe of the present invention, the amount of a medical solution remaining in the syringe barrel after administration can be overwhelmingly decreased compared with the conventional medicine syringe. In the present invention, the amount of the medicinal solution that remains in the syringe barrel may preferably be 10 μL or smaller upon completion of injection of the medicinal solution by sliding the piston via the plunger rod.

The syringe barrel 2 may preferably be provided at a flange-side end portion thereof with an outwardly-flared opening portion 26 to facilitate the handling upon insertion of the piston 3 into the chamber 211 of the main body 21. The medicine syringe according to the present invention has an extremely small capacity of not greater than 0.5 mL in terms of total capacity, and the diameter of the chamber 211 of the main body 21 is, for example, from 1.0 to 3.0 mm. The effect of the outwardly-flared opening portion 26 to facilitate the insertion of the piston 3 is, therefore, extremely significant. The outermost diameter of the outwardly-flared opening portion 26 may preferably be from 3 to 5 times or so the diameter of the piston 3, and the flare angle of the outwardly-flared opening portion 26 may preferably be from 5 to 45 degrees or so with respect to the axial direction of the syringe barrel 2.

In the first embodiment shown in FIG. 1, the stroke of the piston 3 to inject the medical solution extends from the lower end of the reduced diameter portion 29 to the upper end of the outwardly-flared opening portion 26. The stroke of the piston 3 upon administration of an extremely small amount of a medical solution by the medicine syringe according to the present invention may be designed to range from 20 to 100 mm for an internal capacity of from 0.02 to 0.5 mL.

The piston 3 may be a cylindrical piston having three ribs formed at equal intervals on a sliding surface thereof as shown in FIG. 1, or may be in a cylindrical form without such rib or ribs. Any piston shape can be used insofar as it is commonly employed in syringes. However, the medicine syringe itself is substantially reduced in dimensions, and the piston itself is required to have a size, for example, of from 1.1 to 3.5 mm or so in diameter and from 1.5 to 3.0 mm or so in length. Therefore, the piston may preferably be in such a shape as enabling its manufacture with a good yield despite such a miniature size.

The plunger rod 4 is provided at an end portion thereof with the piston 3, and is constructed of a plunger flange portion 42 and a rod-shaped plunger stem portion 41. The plunger flange portion 42 is arranged at an opposite end portion of the plunger rod 4 to facilitate the operation of the plunger rod, and the plunger stem portion 41 connects these piston 3 and plunger flange portion 42 to each other. To complement the strength of the plunger rod 4, plunger reinforcements 43 may preferably be arranged over a joint area between the plunger stem portion 41 and the plunger flange portion 42. As the plunger rod 4 is also reduced in dimensions, the plunger reinforcements 43 serve to reinforce the joint area and to avoid damage to the plunger rod 4.

In the first embodiment shown of FIG. 1, the plunger stem portion 41 is formed in a cylindrical shape. The plunger stem portion 41 may be in such a cylindrical shape as shown in the figure, or may have a cruciform or the like in cross-section as conventionally used in syringes.

The plunger flange portion 42 may preferably be in a plate shape. Its shape can be designed as desired, obviously including a circular plate shape. However, the formation of the plunger flange portion 42 in a polygonal shape such as an oval plate shape or hexagonal plate shape is preferred because the polygonal shape can prevent the plunger rod 4 from rolling on a flat surface. As the size of the plunger flange portion 42, it is preferred to form the plunger flange portion 42 in the shape of a circle, the diameter of which is from 10 to 30 mm or so, or a polygon or like inscribed in the circle such that the plunger flange portion 42 can be readily handled by the thumb which is generally employed for the operation of the plunger rod 4.

In the medicine syringe 1 shown by way of example in FIG. 1, the plunger reinforcements 43 are arranged as many as four over the joint area between the plunger stem portion 41 and the plunger flange portion 42. Described specifically, four triangular plates—the widths of which gradually increase from the side of a position on the plunger stem portion 41, said position being approx. 2/3 the way down from the end portion where the piston 3 is arranged, to the plunger flange portion 42—are arranged at intervals of 90 degrees, although the plunger reinforcements shall not be limited to these shape, number and arrangement.

For the connection of the piston 3 and the plunger rod 4, it is possible to adopt the threaded engagement method or integral molding method employed in conventional syringes. Nonetheless, the piston and plunger rod used in the present invention are very small so that the threaded engagement method is generally difficult to assure sufficient connection strength. It is, therefore, preferred to connect the piston 3 and the plunger rod 4 together by a method that integrally molds a piston plunger rod, an integrated unit of a piston and a plunger rod, with a single material or by another method that forms beforehand one of the piston and plunger rod, inserts it in a mold for molding the other one of the piston and plunger rod, and then conducts injection molding or compression molding.

Figure 2:
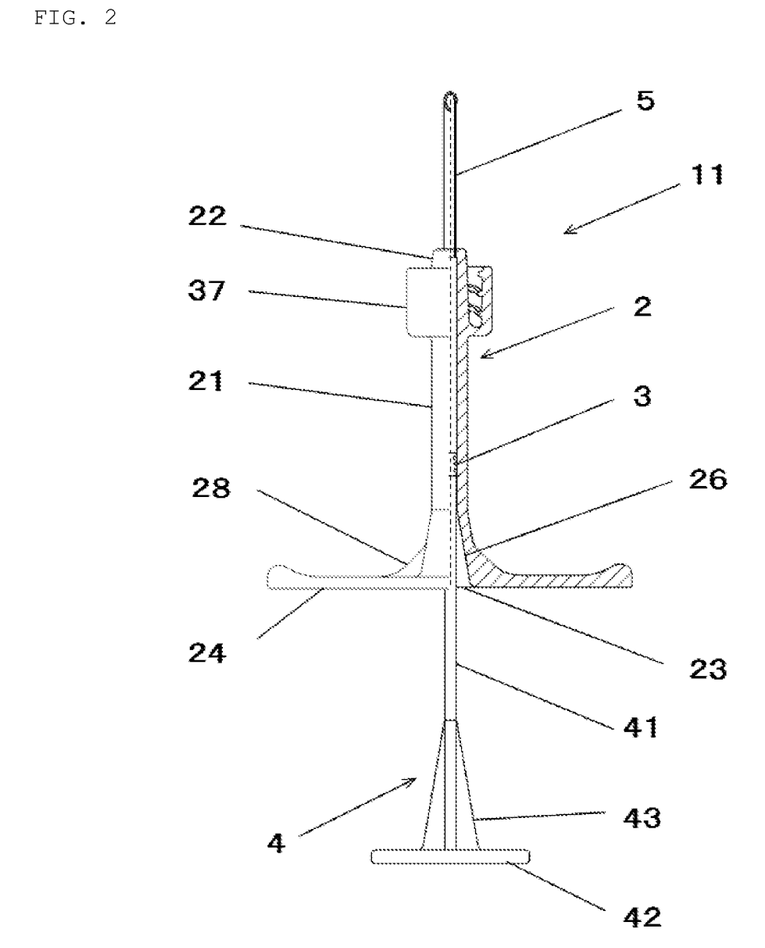
FIG. 2 is a partly cross-sectional schematic view of a medicine syringe according to a second embodiment of the present invention.

With reference to FIG. 2, a medicine syringe according to a second embodiment of the present invention will hereinafter be described. The medicine syringe 11 shown by way of example in FIG. 2 has the same construction as the medicine syringe 1 shown in FIG. 1 except that a syringe needle 5 is integrally fitted in the injection nozzle portion 22 of the syringe barrel 2. The syringe needle 5 is generally made of a metal such as stainless steel. As a fitting method of a syringe needle, it is known to concurrently insert the syringe needle in a mold upon injection molding of a syringe barrel to integrate the syringe needle with the syringe barrel or to bond the syringe needle to the syringe barrel with an adhesive or the like after the molding of the syringe barrel. In the second embodiment shown in FIG. 2, the syringe needle 5 is integrally fitted in the injection port 25 (see FIG. 1). As the syringe needle 5 is integrally melt-welded at a proximal end portion thereof with an inner wall of the injection port 25, the proximal end portion serves to prevent the piston 3 from falling off the injection port 25 like the above-described reduced diameter portion 29 (see FIG. 1). The medicine syringe 11 shown by way of example in FIG. 2, therefore, does not need to additionally arrange the reduced diameter portion 29 unlike the medicine syringe 1 shown by way of example in FIG. 1. It is to be noted that a Luer lock fitting, specifically a female Luer lock fitting 37 in FIG. 2 is different in function from the female Luer lock fitting 27 in FIG. 1 and is used to fixedly secure a needle shield (not shown) for the protection of the syringe needle 5.

In the second embodiment shown in FIG. 2, a medicinal solution remains in the bore of the syringe needle 5 instead of the hollow bore in the reduced diameter portion 29. The second embodiment may, therefore, look to allow the medicinal solution to remain in a greater amount than the first embodiment. However, the medicine syringe 1 of the first embodiment shown in FIG. 1 also requires to additionally fit a syringe needle (not shown) upon use, and therefore, cannot avoid a medicinal solution to remain in the bore of the syringe needle either. As a matter of fact, the occurrence of a gap is known to be unavoidable at a joint between the syringe nozzle and the injection nozzle portion 22 in the medicine syringe 1 shown by way of example in FIG. 1 although the gap is small. As a consequence, the medicine syringe 11 according to the second embodiment shown in FIG. 2 is smaller in the amount of the medical solution that remains including the medical solution remaining in the bore of the syringe needle 5. Moreover, the medicine syringe 11 according to the second embodiment shown in FIG. 2 has another merit in that immediate use is possible because no fitting of a syringe needle is needed upon use.

As a material for use in the syringe barrel that makes up the medicine syringe according to the present invention, a synthetic resin is preferred. Usable examples include cyclic olefin resins, polycarbonates, polypropylene, polyethylene terephthalate, polyethylene naphthalate, and the like, all of which are commonly employed in medical instruments. Cyclic olefin resins are preferred particularly from the standpoints of dissolution characteristics, transparency, mechanical strength and the like.

As a material for use in the piston that also makes up the medicine syringe according to the present invention, it is possible to employ an elastomer useful as a material for pistons in syringes which have been conventionally employed for medicines. Illustrative synthetic rubbers include butyl rubber (IIR), chlorinated butyl rubber (CIIR), brominated butyl rubber (BIIR), partially-crosslinked IIR, polybutadiene rubber (BR), polyisoprenes rubber (IR), ethylene-propylene-diene terpolymer rubber (EPDM), styrene-butadiene copolymer rubber (SBR), acrylic rubber (ACM), acrylonitrile butadiene rubber (NBR), and the like. Illustrative thermoplastic elastomers include polyisobutylene-based thermoplastic elastomers (SIBS), styrene-based elastomers such as styrene-butadiene-styrene (SBS) based copolymers, styrene-ethylene-butylene-styrene (SEBS) based copolymers and styrene-isoprene-styrene (SIS) based copolymers, and olefinic elastomers such as ethylene-propylene-non-conjugated diene monomer (EPDM) based copolymers and ethylene-propylene (EPM) based copolymers. Among these, butyl rubber, chlorinated butyl rubber and polyisobutylene-based elastomer are preferred for gas barrier properties, dissolution characteristics and the like. The piston may preferably be laminated, at each of its sliding surface with the syringe barrel and its top wall to be brought into contact with a medical solution, with a film of a fluorinated resin such as PTFE.

As a material for use in the plunger rod that also makes up the medicine syringe according to the present invention, it is possible to employ one useful as a material for pistons in syringes which have been conventionally used for medicines. Examples include synthetic resins, for example, general-purpose plastics such as polyethylene and polypropylene. Relatively soft materials such as polymethylpentene and soft polypropylene can also be used. With such a material, a piston plunger rod which is an integrated unit of a piston and a plunger rod can be formed for use in the present invention.

The present invention will hereinafter be described in further detail based on Examples.

Example 1

Using a cyclic olefin resin (CZ resin; product of Daikyo Seiko, Ltd.), a syringe barrel was formed with the inner diameter and stroke presented in Table 1-1 and the shape shown in FIG. 1. The outer diameter of a main body of the syringe barrel was set at 4.2 mm, and a reduced diameter portion for preventing a piston from falling off an injection port was dimensioned at 1.0 mm in length and 0.8 mm in inner diameter. A piston and plunger rod were combined with the thus-obtained syringe barrel to produce a test syringe of this example. The piston was made of chlorinated butyl rubber and was laminated at each of its sliding surface with the syringe barrel and its solution-contacting surface with a PTFE resin film, while the plunger rod was made of polypropylene and was integrally molded with the piston.

Examples 2 to 6

Syringe barrels, which had the inner diameters and strokes presented in Table 1-1, respectively, and the shape of FIG. 1 (Examples 2, 4 and 6) or the shape of FIG. 2 (Examples 3 and 5), were formed as in Example 1. Similar to Example 1, each of those syringe barrels was 4.2 mm in the outer diameter of a main body. Reduced diameter portions of the syringe barrels of Examples 2 and 4 were dimensioned as in Example 1. The syringe barrel of Example 6 was similar to the syringe barrel of Example 1 except that its reduced diameter portion was dimensioned at 2.0 mm in length. In each of the syringe barrels of Examples 3 and 5, a syringe needle made of stainless steel (equivalent to 29 GTW) was integrally fitted in an injection port as shown in FIG. 2. The syringe needle had dimensions of 25.0 mm in length and 0.2 mm in inner diameter. With the respective syringe barrels formed as described above, laminated pistons and plunger rods made of the same material as that used in Example 1 were combined to produce test syringes of Examples 2 to 6. It is, however, to be noted that the outer diameters of the pistons and the lengths of the plunger rods were changed according to the dimensions of the corresponding syringe barrels.

Comparative Examples 1 and 2

Syringe barrels, which had the inner diameters and strokes presented in Table 1-2, respectively, and the shape of FIG. 1, were formed as in Example 1. Their main bodies were dimensioned at 4.2 mm in outer diameter, and their reduced diameter portions were dimensioned at 1.0 mm in length and 0.8 mm in inner diameter (the syringe of Comparative Example 1) or at 2.0 mm in length and 0.8 mm in outer diameter (the syringe of Comparative Example 2). With those syringe barrels, laminated pistons and plunger rods made of the same material as that used in Example 1 were combined, respectively, to produce test syringes. It is, however, to be noted that the outer diameters of the pistons and the lengths of the plunger rods were changed according to the dimensions of the corresponding syringe barrels.

Comparative Examples 3 and 4

Using the same resin as the syringe barrel in Example 1, syringe barrels, which had the inner diameters and strokes presented in Table 1-2, respectively, and the shape of the conventional syringe barrel shown in FIG. 3, were formed. The syringe barrels were both dimensioned at 11.5 mm in outer diameter, and their injection nozzle portions were both dimensioned at 10 mm in length and 1.3 mm in inner diameter. With those syringe barrels, laminated pistons and plunger rods made of the same material as that used in Example 1 were combined, respectively, to produce test syringes. It is, however, to be noted that the outer diameters of the pistons and the lengths of the plunger rods were changed according to the dimensions of the corresponding syringe barrels.

Injection Amount Test and Remaining Medical-Solution Volume Test

On an outer surface of each test syringe produced as described above, five scale markings were printed at equal intervals of ⅕ of the capacity of the syringe, and the weight of the syringe itself was measured by an electronic analytical balance ("AEG-320", trade name; product of Shimadzu Corporation). The syringe was next filled with purified water in an amount a little greater than 20% of its capacity with care such that no air bubbles were included. The syringe was then left still for 24 hours to provide the test syringe in which the purified was filled in the amount a little greater than 20% of its capacity. Using each syringe provided as described above, the plunger rod was first pushed in until the distal end of the piston reached the first scale marking to discharge extra purified water. While keeping close watch on the individual scale marking, the water in the syringe was then injected scale marking by scale marking into weighing vials, respectively. Based on the weight changes of the respective weighing vials, the injection amounts corresponding to the respective scale markings were measured by the electronic analytical balance. After completion of the injection, the weight of the syringe was measured again, and based on its difference from the weight of the syringe itself as measured at the beginning, the amount of the water remaining in the syringe was calculated. The evaluation results are presented in Tables 1-1 and 1-2.

TABLE 1-1

Evaluation Results (Examples)

| | Ex. 1 | Ex. 2 | Ex. 3 | Ex. 4 | Ex. 5 | Ex. 6 |
|---|---|---|---|---|---|---|
| Capacity (mL) | 0.02 | 0.05 | 0.05 | 0.10 | 0.10 | 0.50 |
| Inner diameter (mm) | 1.1 | 1.2 | 1.2 | 1.6 | 1.6 | 3.0 |
| Stroke (mm) | 21.1 | 44.2 | 44.2 | 50.0 | 50.0 | 70.1 |
| Injection amount per scale marking (mL) | 0.0038 | 0.0100 | 0.0101 | 0.0200 | 0.0200 | 0.1004 |
| | 0.0040 | 0.0101 | 0.0100 | 0.0201 | 0.0201 | 0.1002 |
| | 0.0042 | 0.0102 | 0.0101 | 0.0200 | 0.0200 | 0.0998 |
| | 0.0041 | 0.0100 | 0.0101 | 0.0201 | 0.0200 | 0.0999 |
| | 0.0041 | 0.0101 | 0.0101 | 0.0200 | 0.0201 | 0.0997 |
| Standard deviation ($\times 10^{-5}$) | 15.2 | 8.4 | 4.5 | 5.5 | 5.5 | 29.2 |
| Amount of remaining water (μL) | 0.51 | 0.52 | 0.79 | 0.52 | 0.80 | 1.11 |
| Remarks | | Fitted with syringe needle | | Fitted with syringe needle | | Length of reduced diameter portion: 2 mm |

TABLE 1-2

Evaluation Results (Comparative Examples)

| | Comp. Ex. 1 | Comp. Ex. 2 | Comp. Ex. 3 | Comp. Ex. 4 |
|---|---|---|---|---|
| Capacity (mL) | 0.01 | 1.0 | 1.0 | 3.0 |
| Inner diameter (mm) | 1.0 | 3.0 | 8.5 | 8.5 |
| Stroke (mm) | 12.7 | 141.5 | 17.6 | 52.9 |
| Injection amount per scale marking (mL) | 0.0014 | 0.2015 | 0.2012 | 0.6235 |
| | 0.0018 | 0.2212 | 0.1993 | 0.6537 |
| | 0.0023 | 0.1984 | 0.1987 | 0.5887 |
| | 0.0017 | 0.2002 | 0.2005 | 0.6152 |
| | 0.0028 | 0.2002 | 0.2008 | 0.5649 |
| Standard deviation ($\times 10^{-5}$) | 55.2 | 951.2 | 105.6 | 3392.4 |
| Amount of remaining water (μL) | 0.50 | 1.13 | 13.5 | 13.6 |
| Remarks | | Length of reduced diameter portion: 2 mm | Conventional shape | Conventional shape |

As presented in Tables 1-1 and 1-2, it was confirmed that with each of the syringes of Examples 1-6, the injection amounts corresponding to the respective scale markings as injected separately in five portions did not vary much and accurate injection was hence feasible in precise amounts. It was also confirmed that with each of the syringes of the Examples, the amount of remaining water was considerably decreased than with the syringes of the conventional shape in Comparative Examples 3 and 4. This means that the medicine syringe according to the present invention makes it possible to perform economically-excellent administration of a medicinal solution compared with conventional medicine syringes.

To meet the desire in recent years for an easy-to-use medicine syringe that has a total capacity of not greater than 0.5 mL and makes it possible to appropriately administer a medical solution in extremely small volume or volumes, the present invention can provide a medicine syringe in which a movement of a piston upon administration of a medicinal solution has a sufficiently long stroke, and as a consequence, the medicine syringe can assure the accuracy of a dose the importance of which has become greater as a result of an increase in the medicinal efficiency per unit volume of the medical solution, and to cope with an increase in the price of the medical solution per unit volume, can also make still smaller the amount of the medical solution remaining in the syringe after use. The present invention is, therefore, expected to find wide-spread utility.

The invention claimed is:

1. A medicine syringe comprising a syringe barrel, a piston and a plunger rod,
    said syringe barrel being provided with:
        a cylindrical main body defining therein a chamber to be filled with a medical solution, an injection nozzle portion for injecting the medical solution, said injection nozzle portion being formed at an end portion of the main body that comprises an end wall, and defining therein a hollow bore in communication with the chamber, with the injection nozzle portion further comprising an injection port extending through the end wall for injecting out the medical solution from the chamber through the injection nozzle portion, and an opening being formed at an opposite end portion of the main body for receiving the piston and plunger, and
        a flange portion,
    said plunger rod being in a form of a rod having the piston arranged at an end portion thereof and a plunger flange formed at an opposite end portion thereof, wherein:
    the chamber in the main body and said hollow bore in the injection nozzle portion have a total capacity of not greater than 0.5 mL,
    a reduced diameter portion is defined by the injection port, and the chamber and hollow bore have a same diameter up to the reduced diameter portion,
    the injection nozzle portion is configured so that an injection needle to be used with the medical syringe is held in the injection port with a proximal end of the injection needle not extending into the injection nozzle portion beyond the reduced diameter portion, and
    the chamber and hollow bore are formed such that the piston is slidable in a range of from 20 to 100 mm and allowed to slide liquid-tight into the hollow bore of the injection nozzle portion beyond the chamber located in the main body
    wherein the cylindrical main body and the injection nozzle portion are of unitary construction.

2. The medicine syringe according to claim 1, wherein the structure that enables a syringe needle to fit the injection nozzle portion is a Luer lock fitting for fixedly securing the syringe needle.

3. The medicine syringe according to claim 1, further comprising a syringe needle integrally fitted to the injection nozzle portion.

4. The medicine syringe according to claim 3, wherein the injection nozzle portion is further provided with a Luer lock fitting for fixedly securing a needle shield to protect the syringe needle.

5. The medicine syringe according to claim 1, wherein no more than 10 μL of the medical solution remains in the syringe barrel upon completion of an injection of the medical solution by sliding the piston.

6. The medicine syringe according to claim 1, wherein the flange portion of the syringe barrel extends out over a length of from 15 to 50 mm from the opposite end portion.

7. The medicine syringe according to claim 1, wherein the plunger rod and piston are integrally molded.

8. The medicine syringe according to claim 1, further comprising a main body reinforcement formed over a joint area between the main body and the flange portion.

9. The medicine syringe according to claim 1, wherein the syringe barrel is formed of a cyclic olefin resin.

* * * * *